United States Patent
Polifroni

(10) Patent No.: US 6,854,199 B2
(45) Date of Patent: Feb. 15, 2005

(54) LAYERED ARCH SUPPORT

(76) Inventor: Joseph Paul Polifroni, c/o 261 N. Hwy. 101, Solona Beach, CA (US) 92075

( * ) Notice: Subject to any disclaimer, the term of this patent is extended or adjusted under 35 U.S.C. 154(b) by 61 days.

(21) Appl. No.: 10/112,199

(22) Filed: Mar. 27, 2002

(65) Prior Publication Data

US 2003/0061736 A1 Apr. 3, 2003

Related U.S. Application Data

(63) Continuation-in-part of application No. 29/150,950, filed on Oct. 24, 2001, now Pat. No. Des. 475,184, which is a continuation-in-part of application No. 09/965,995, filed on Sep. 28, 2001, now Pat. No. 6,557,273.

(51) Int. Cl.7 .............................. A43B 7/14; A43B 7/16; A43B 13/38; A43B 23/00; A61F 5/14
(52) U.S. Cl. ............................. 36/44; 36/145; 36/172; 36/173; 36/178
(58) Field of Search ..................... 36/145, 166, 173, 36/178, 181, 180, 154, 160, 172, 174, 176, 44, 91, 93, 28, 30 R, 31, 147

(56) References Cited

U.S. PATENT DOCUMENTS

| | | | |
|---|---|---|---|
| 1,095,849 A | * | 5/1914 | Good ........................... 36/145 |
| 1,426,258 A | * | 8/1922 | Burns .......................... 36/173 |
| 2,408,792 A | | 10/1946 | Margolin |
| 2,486,653 A | | 11/1949 | Hukill |
| 2,821,032 A | | 1/1958 | Helfet |
| 3,081,774 A | | 3/1963 | Lelyveld |
| 3,135,265 A | | 6/1964 | Holzman |
| 3,306,967 A | | 2/1967 | Turkewitsch |
| 3,333,353 A | | 8/1967 | Garcia |
| 3,543,765 A | | 12/1970 | Alzner |
| 3,985,853 A | | 10/1976 | Weisberg |
| 4,187,620 A | | 2/1980 | Selner |
| 4,541,184 A | | 9/1985 | Leighton |
| 4,571,857 A | | 2/1986 | Castellanos |
| 4,694,590 A | | 9/1987 | Greenawalt |
| 4,702,255 A | | 10/1987 | Schenkl |
| 4,718,179 A | | 1/1988 | Brown |
| 4,908,964 A | * | 3/1990 | Deem ........................... 36/93 |
| 4,972,612 A | | 11/1990 | Prukop et al. |
| 5,216,825 A | * | 6/1993 | Brum ........................... 36/44 |
| 5,282,326 A | | 2/1994 | Schroer, Jr. et al. |
| 5,285,583 A | * | 2/1994 | Aleven ......................... 36/44 |
| 5,359,791 A | | 11/1994 | Prahl et al. |
| 5,394,626 A | | 3/1995 | Brown |
| 5,463,824 A | | 11/1995 | Barna |
| 5,611,153 A | | 3/1997 | Fisher et al. |
| 5,636,456 A | | 6/1997 | Allen |
| 5,642,575 A | * | 7/1997 | Norton et al. ............... 36/28 |
| 5,940,994 A | | 8/1999 | Allen |
| 6,042,759 A | | 3/2000 | Marshall |
| 6,247,250 B1 | | 6/2001 | Hauser |
| 6,263,592 B1 | * | 7/2001 | Chen ........................... 36/44 |

* cited by examiner

Primary Examiner—Anthony Stashick
(74) Attorney, Agent, or Firm—Stephen C. Beuerle; Procopio Cory Hargreaves & Savitch LLP

(57) ABSTRACT

An arch support device has a lower layer of a semi-rigid material shaped to conform to the arch of a wearer's foot and to provide an arch supporting function when inserted in a shoe, a second layer of cushioning material such as foam secured to the upper face of the lower layer; and a third, cover layer of pliable material secured over the second layer. At least one of the lower and foam layers is of variable thickness.

9 Claims, 3 Drawing Sheets

LAYERED ARCH SUPPORT

CROSS-REFERENCE TO RELATED APPLICATIONS

This application is a Continuation-In-Part of application Ser. No. 09/965,995 filed Sep. 28, 2001, now U.S. Pat. No. 6,557,273, and Design patent application Ser. No. 29/150,950 filed Oct. 24, 2001, now U.S. Pat. No. D475,184.

BACKGROUND OF THE INVENTION

The present invention relates to arch or foot supports for insertion in footwear in order to provide better comfort and more correct positioning and support of the wearer's feet.

Many individuals who are on their feet or walking for significant periods of time encounter the problems of pain and sore feet usually associated with uncomfortable footwear. Such problems often arise as a result of insufficient arch support in conventional shoes and other footwear. Thus, various types of shoe inserts have been devised in order to alleviate such problems. Some inserts consist only of a foam or padded cushion member or insole, and provide no arch support. It is also known to provide more sophisticated arch supports formed of molded rigid or semi-rigid materials, such as plastic, and these are sometimes custom-fitted to the individual, which makes them relatively expensive. Also, the rigid nature of such arch supports can itself lead to some discomfort. In some cases, a leather upper layer is applied to the top surface of the arch support, but this device may still not be particularly comfortable in some cases. A layered arch support device is also known which has a lower, rigid plastic layer, a second or core layer of foam material, and an upper leather layer. However, this becomes fairly thick and bulky at the toe and may cause problems in inserting the foot into the shoe.

SUMMARY OF THE INVENTION

It is an object of the present invention to provide a new and improved arch support for insertion in footwear.

According to one aspect of the present invention, an arch support device is provided, which comprises a first, lower layer of a semi-rigid material shaped to conform to the arch of a wearer's foot and to provide an arch supporting function when inserted in a shoe, the lower layer having a lower face for facing the sole of an item of footwear and an upper face, a second layer of cushioning material secured to the upper face of the lower layer, and a third, cover layer of pliable material secured over the second layer, the device having a heel region at one end, and arch region, and a toe region at an opposite end, at least one of the first and second layers being of variable thickness.

The cover layer may be of a relatively smooth, moisture-resistant material such as leather or fabric, while the cushioning layer may be of foam. In an exemplary embodiment, the lower layer is of semi-rigid, molded plastic material. With this arrangement, the lower layer provides adequate support for the arch of the foot, while the upper cushioning and cover layers make the arch support more comfortable for the wearer.

The arch support device will be made for fitting left and right footwear, and in different sizes to accommodate the standard range of footwear sizes. The device may have an outer periphery designed to substantially match that of the sole of the footwear in which it is to be inserted, or may extend over only part of the sole, from the heel region up to a point adjacent the wearer's toes. The second, cushioning layer and upper cover layer may be of slightly larger dimensions than the semi-rigid, arch support layer such that a cushioning rim portion projects a short distance beyond the rim of the lower layer, for added comfort of the wearer, such that their feet will not bear against any more rigid part of the support device. In one exemplary embodiment, the arch support layer may be of shorter length than the foam and upper layers, with the foam and upper layers protruding beyond the toe end of the arch support layer, for cushioning the ends of the toes.

The overall thickness of the three layer assembly may differ from the heel to the toe, with the thickness being greater at the heel, arch, and sulcus region of the foot than the toe. This variation in thickness ensures that region of maximum thickness are associated with the maximum pressure regions of the wearer's sole when standing or walking. At the same time, the reduced thickness at the toe enables the foot to enter the shoe more easily with the arch support in place.

The lower face of the arch support layer may be smooth, or may have surface roughening or indents to grip the insole of the shoe. In one exemplary embodiment, the lower face may have a waffle-shaped pattern of indents similar to a tire tread, for increased resistance to slipping. This may extend over only part of the lower face, for example from the toe to a point just beyond the arch. The heel may have a shaped, roughened area for further slip resistance. The lower layer may have holes for receiving adhesive extending over the upper surface to secure the second layer more firmly to the lower layer.

The arch support device of this invention will provide a good support for the arch of the wearer's foot while still providing cushioning and comfort in regions of maximum pressure. The device is relatively inexpensive to manufacture and can be made in all appropriate arch support sizes.

BRIEF DESCRIPTION OF THE DRAWINGS

The present invention will be better understood from the following detailed description of some exemplary embodiments of the invention, taken in conjunction with the accompanying drawings in which like reference numerals refer to like parts and in which.

DETAILED DESCRIPTION OF THE DRAWINGS

Figure 1:
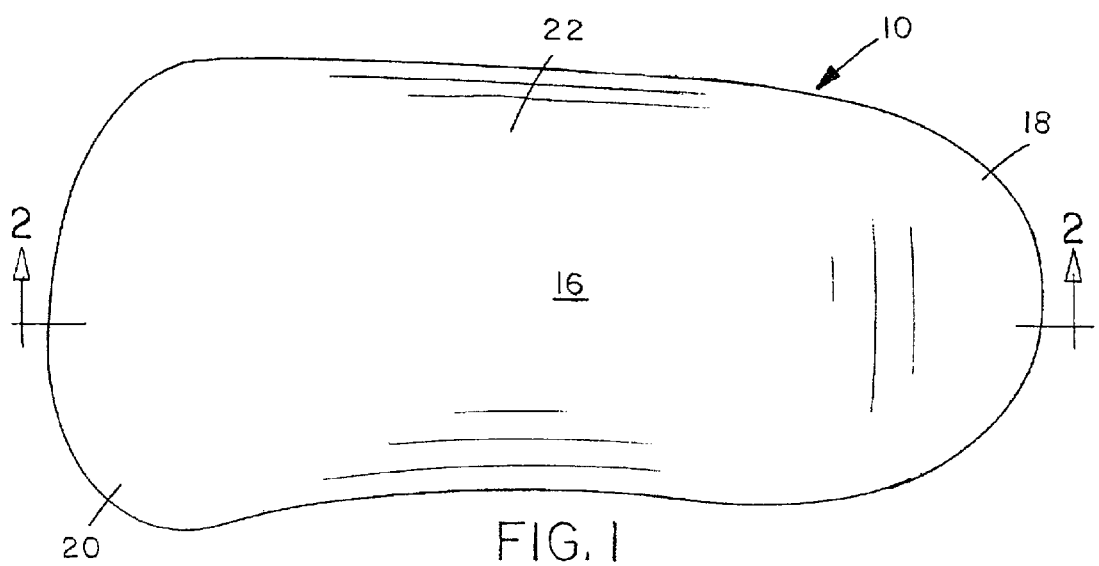
FIG. 1 is a top plan view of an arch support device according to an exemplary embodiment of the invention.

FIGS. 1 to 4 of the drawings illustrate an arch support device 10 according to an exemplary embodiment of the invention. The device 10 basically comprises a lower layer 12 of rigid or semi-rigid material, a core or inner layer 14 of cushioning material such as foam, and an upper, cover layer 16. The lower layer 12 has a predetermined contour shaped to conform to the contour of at least part of the sole of a foot, extending at least from a heel region 18 up to a metatarsal rise region 20 and including the arch region 22. The arch support device may be made in a ¾ foot length or full foot length, as is known in the field for conventional one layer arch supports.

In one specific example of the arch support device of FIGS. 1 to 4, the lower layer 12 was of EVA plastic or other relatively hard or rigid plastic material, the core or middle layer 14 was of foam material, and the cover layer 16 was of leather. The three layers were adhered together by a suitable adhesive.

Figure 2:
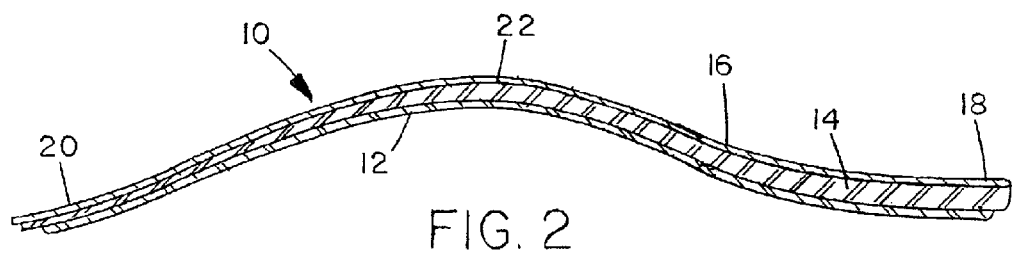
FIG. 2 is across-sectional view of the arch support device on the lines 2—2 of FIG. 1.
Figure 4:
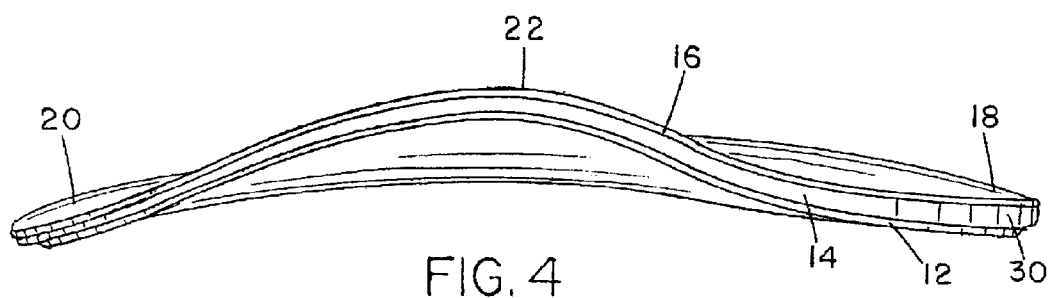
FIG. 4 is a side elevation view of the arch support device.

As indicated in FIGS. 2 and 4, the core layer 14 of foam material is of tapering thickness along the length of device 14, with the thickest region 30 corresponding to the heel region 18. The region 30 is thicker than the other two layers, to provide sufficient cushioning for the wearer's foot from the relatively hard surface of the lower, arch supporting layer 12.

Figure 3:
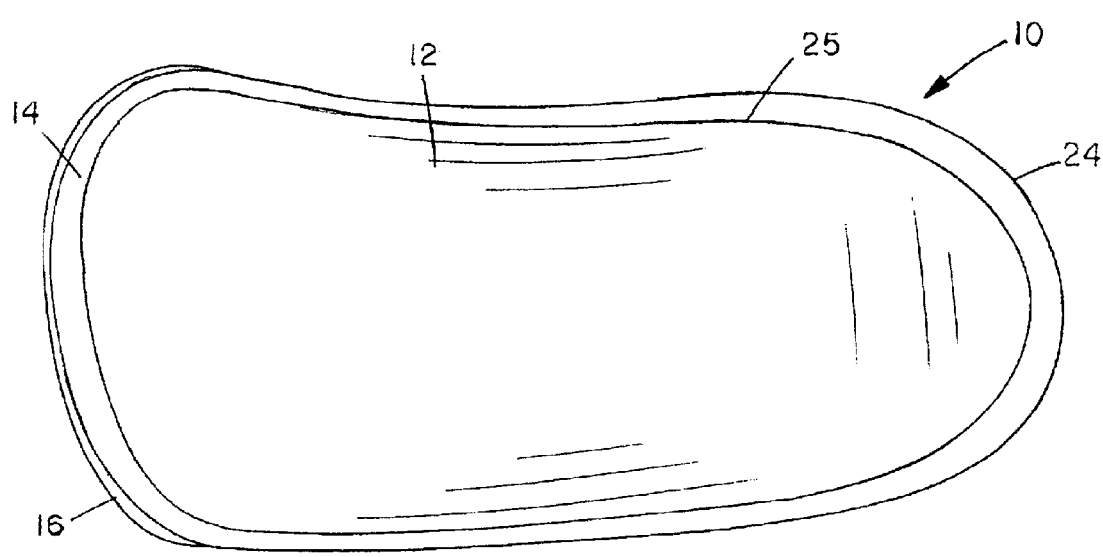
FIG. 3 is a bottom plan view of the arch support device.

The foam layer then tapers down to minimum thickness at the toe region or metatarsal rise. The reduction in thickness from the heel region to the toe region may be of the order of 25% to 75%. The thickness of the foam layer 14 in the heel region may be of the order of 5 to 10 mm., while the thickness in the toe region may be 0.5 to 2 mm. As indicated in FIGS. 2 and 3, the foam and cover layers have an outer peripheral edge 24 which projects outwardly beyond the periphery 25 of the lower, rigid or semi-rigid layer 12, forming a projecting rim of cushioning material around the entire periphery of the device. This provides for added comfort of the wearer, since the edge of their foot will not contact the relatively hard rim or periphery of the lower layer even when the cushion and cover layers are pressed down during wear.

The three layer construction with a central core layer of foam material provides for adequate arch support with increased comfort. The user's foot will be supported properly in the arch region, but the foam cushioning layer will avoid pressing of the sole of the foot directly against the relatively rigid lower layer which is contoured for the desired supporting function. The maximum thickness of foam in the heel region gives more cushioning in the area where maximum pressure is normally applied, while the reduced thickness foam layer in the toe region gives more support and allows easier insertion of the foot into the shoe.

The thickness of foam layer 14 may be uniform from the heel region up to the arch region, and then taper gradually from the arch to the toe, where less cushioning is necessary or may taper uniformly from the heel to the toe. The thinner foam portion in the toe region assists in support in this area, while also allowing the foot to enter the shoe more readily when the device is in place.

Figure 5:
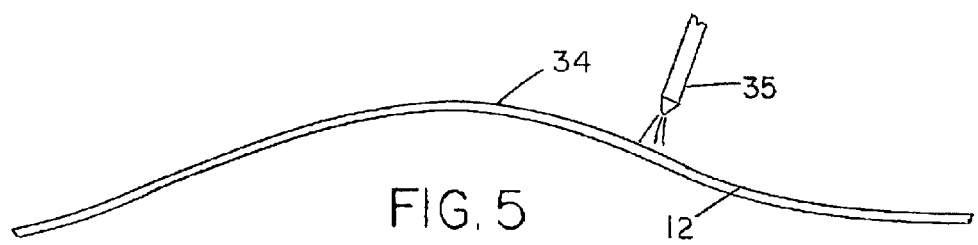
FIG. 5 is a side view of the lower layer of the arch support device showing roughening of the upper surface during manufacture.
Figure 6:
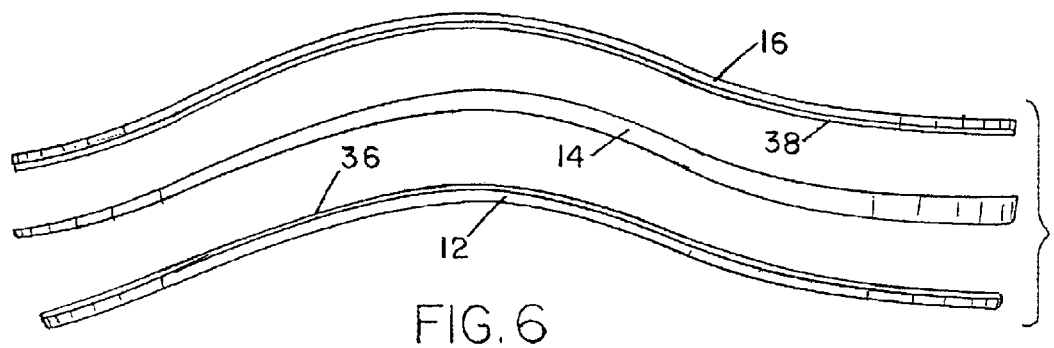
FIG. 6 is a side view of the separated layers showing application of adhesive prior to adhering the layers together.

FIGS. 5 and 6 illustrate steps in a method of manufacturing the arch support device of FIGS. 1 to 4. In this method, the arch support or lower layer 12 of rigid or semi-rigid plastic material is first molded into the appropriate shape and contour. The upper surface 34 of this layer is then roughened, for example by sand blasting using a sand blasting tool 35, as indicated in FIG. 5. Once the entire upper surface has been roughened, a layer 36 of a suitable adhesive is applied to the upper surface, as illustrated in FIG. 6. A layer 38 of adhesive is also applied to the lower surface of the cover layer 16, and the three layers are subsequently adhered together.

FIGS. 7 to 10 of the drawings illustrate an arch support device 40 according to another embodiment of the invention. The device 40 comprises a lower layer 42 of semi-rigid material, a core or second layer 44 of cushioning material such as foam, and an upper, cover layer 45. The lower layer 42 has a predetermined contour shaped to conform to the contour of at least part of the sole of a foot, and the device may be made in a ¾ foot length or full foot length, as is known in the field for conventional one layer arch supports.

In one specific example of the arch support device of FIGS. 7 to 10, the lower layer was of semi-rigid plastic material having a Shore D durometer hardness in the range from 25 to 40, and suitably in the range of 30 to 35. The second or core layer 44 was of foam, and the upper layer 45 was of leather or fabric material. The three layers were adhered together with a suitable adhesive, with the upper surface of the first or lower layer 42 suitably being scratched or roughened to provide better adhesion.

Figure 7:
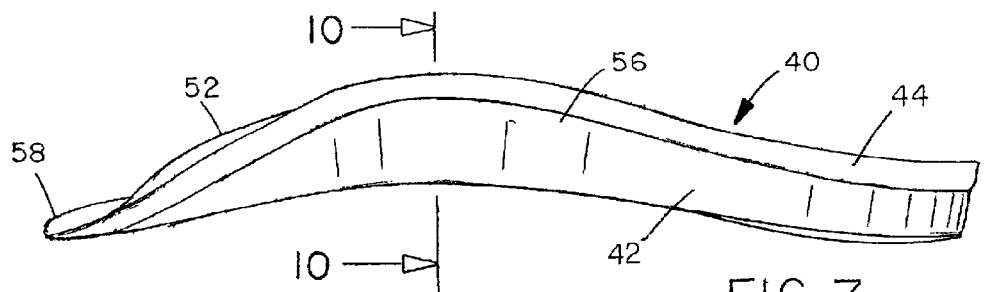
FIG. 7 is a side view of an alternative configuration of the arch support device.
Figure 9:
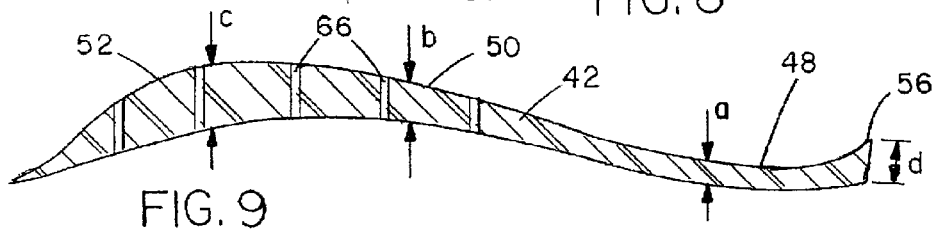
FIG. 9 is a sectional view taken on line 9—9 of FIG. 8, with the cushion layer removed.
Figure 10:
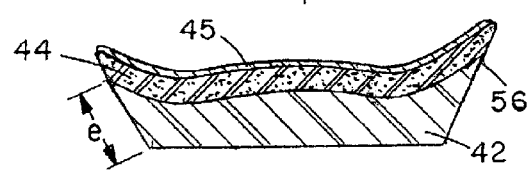
FIG. 10 is a sectional view taken on line 10—10 of FIG. 7.

Unlike the previous embodiment, where the foam layer is of varying thickness, the foam layer 44 in this embodiment is of substantially constant thickness along its length, as indicated in FIG. 7. However, the lower or first layer 42 is of variable thickness. The thickness variation along the central longitudinal axis of the layer 42, as indicated in FIG. 9, varies from a minimum thickness a at the center of heel region 48, a greater thickness b at arch region 50, and a maximum thickness c corresponding to the sulcus region 52 of the foot, designed to engage in the groove of the toes. The thickness tapers back down to a minimum thickness at the toe end 55 of the layer 42. Additionally, the first layer 42 is provided with a thicker, upwardly directed rim 56 around the periphery of the heel and opposite sides of the device, as best illustrated in FIGS. 7, 9 and 10. The rim terminates short of the toe end 55 of the layer 42. Rim 56 is of tapering height, with a minimum height d at the heel end, and a maximum height e at the arch region of the device.

In an exemplary embodiment, the thickness a was in the range of around 0.1 to 0.2 inches, thickness b was in the range 0.2 to 0.4 inches, thickness c was in the range of around 0.3 to 0.5 inches, rim height d was in the range 0.3 to 0.4 inches, and the rim height e at the arch was of the order of 0.5 to 0.8 inches. In one example, the thickness a was around 0.14 inches, thickness b was around 0.30 inches, and the maximum thickness c was around 0.41 to 0.45 inches. The combination of the thickness variation, raised rim, and contour of the upper surface of the lower layer is designed to follow the contour of the undersurface of the wearer's foot, while providing more rigidity and support in the thicker regions.

Figure 8:
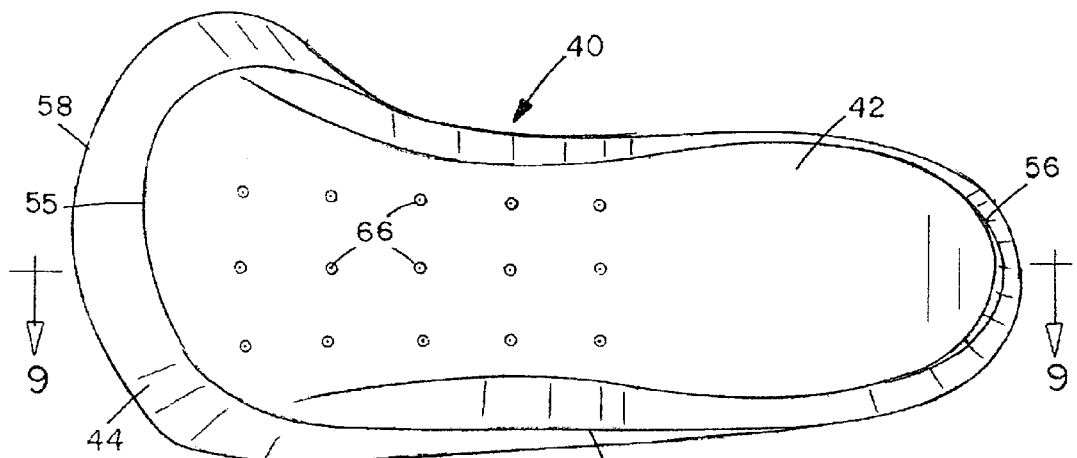
FIG. 8 is a bottom plan view thereof.

The lower surface of the first layer is generally smooth, while the upper face is contoured, as generally indicated in FIGS. 9 and 10, and the pliable foam and cover layers 44 and 45 will adopt the same contour when adhered to the upper surface of layer 42, as indicated in FIG. 10. This will make the device more comfortable since the cushioning will extend up around the sides of the feet and back of the heel. As indicated in FIG. 8, the foam layer 44 and cover layer 45 extend beyond the toe end 55 of layer 42, in the case of a ¾ length insert, up to toe end 58 of the foam layer, so as to provide cushioning for the ends of a wearer's toes. Foam layer 44 also extends slightly beyond the heel end of layer 42, to provide even more cushioning of the heel of the wearer's foot.

Figure 11:
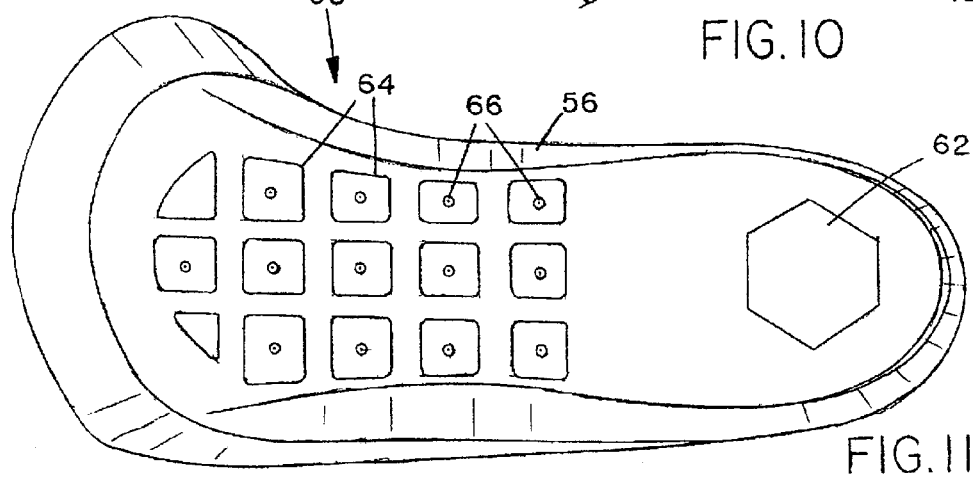
FIG. 11 is a view similar to FIG. 8, but showing a patterned lower surface.

It will be understood that, although the foam layer 44 in this embodiment is of substantially uniform thickness, it may alternatively be of varying thickness similar to foam layer 14 of the previous embodiment, if additional cushioning is required in the heel region, for example. The first or lower layer 42 has a lower surface which may be relatively smooth, as indicated in FIG. 8, with suitable non-slip properties to resist movement or shifting of the device when in the shoe. Alternatively, it may have slip resistant configurations, for example as indicated in FIG. 11, and as shown in my co-pending Design Patent Application No. 29/150,950 filed Oct. 24, 2001, the contents of which are incorporated herein by reference. In the modified lower layer 60 of FIG. 11, the lower surface has a roughened surface region 62 of generally hexagonal shape in the heel region. It also has a waffle-like pattern of generally square or rectangular indents 64 similar to tire treads extending from the arch region to the toe region of the device. Layer 60 is otherwise identical to that of FIGS. 7 to 10, as are the foam layer and cover layer, and like reference numerals have been used as appropriate. The roughened region 62 and indents 64 will provide additional grip against the sole of a shoe into which the device is inserted, reducing the risk of the device slipping or moving around as the wearer walks.

The lower layer may have a series of through holes 66 extending over at least the arch and toe regions, as indicated in FIGS. 8 and 11. The holes 66 provided added ventilation through the device, since the foam and upper layers will also have some porosity. This helps to cool a wearer's foot.

The arch support device of this invention has advantages over known rigid or semi-rigid arch support devices, as well as known cushioning insoles. It will be more comfortable to wear than a conventional arch support device which is substantially rigid and may cause discomfort to the sole of a wearer's foot, while providing better support to a wearer's foot than footwear containing a fully compressible insole. The tapered foam layer of the first embodiment provides more cushioning in the heel region, where maximum pressure is normally applied, with gradual reduction in foam thickness to the toe, for better support. In the second embodiment, added cushioning is provided around the sides and heel of the foot, in view of the upturned rim over which the cushioning and cover layers extend. At the same time, the lower layer is of variable thickness to provide added support where required, specifically at the toe/ball region. At the same time, in both cases, the overall thickness of all layers tapers to a minimum at the toe end. This also makes the device thinner at the toe, so that the foot can enter the shoe more easily.

Although some exemplary embodiments of the invention have been described above by way of example only, it will be understood by those skilled in the field that modifications may be made to the disclosed embodiments without departing from the scope of the invention, which is defined by the appended claims.

I claim:

1. An arch support device, comprising:
a first, lower layer of semi-rigid material shaped to conform to the arch of a wearer's foot and to provide an arch supporting function when inserted in a shoe, the lower layer having a lower face for facing the sole of an item of footwear, an upper face, a heel region at one end, an arch region, and a toe region;
a second layer of cushioning material secured to the upper face of the lower layer;
a third, cover layer of pliable material secured over the second layer;
the lower layer being of variable thickness; and
the upper face of the lower layer being contoured to follow the general contours of at least part of the sole of a wearer's foot, having a generally concave area at the heel region and a convex, raised area extending from the arch region towards the toe region for engaging in a groove of a wearer's toes, the convex, raised area having a thickness greater than the thickness at the heel or arch region.

2. An arch support device, comprising:
a first, lower layer of semi-rigid material shaped to conform to the arch of a wearer's foot and to provide an arch supporting function when inserted in a shoe, the lower layer having a lower face for facing the sole of an item of footwear, an upper face, a heel region at one end, an arch region, and a toe region;
a second layer of cushioning material secured to the upper face of the lower layer;
a third, cover layer of pliable material secured over the second layer;
the lower layer being of variable thickness; and
the lower layer having an outer periphery and opposite sides, and an upturned peripheral rim extending around part of the outer periphery across the heel and at least part of the sides of the lower layer, the second and third layers extending up to the upturned peripheral rim to follow the upturned rim.

3. The device as claimed in claim 1, wherein the lower layer has a first thickness of 0.1 to 0.2 inches in the heel region, a second thickness of 0.2 to 0.3 inches in the arch region, and a third thickness of 0.3 to 0.5 inches in the convex, raised area.

4. The device as claimed in claim 1, wherein the convex, raised area has a first thickness, and the heel region has a second thickness which is about one third of the first thickness.

5. An arch support device, comprising:
a first, lower layer of semi-rigid material shaped to conform to the arch of a wearer's foot and to provide an arch supporting function when inserted in a shoe, the lower layer having a lower face for facing the sole of an item of footwear, an upper face, a heel region at one end, an arch region, and a toe region;
a second layer of cushioning material secured to the upper face of the lower layer;
a third, cover layer of pliable material secured over the second layer;
at least one of the first and second layers being of variable thickness; and
the lower face of the lower layer has a series of indents spaced across at least part of its area to provide a slip-resistant, gripping portion.

6. The device as claimed in claim 5, wherein the indents are of rectangular cross section and are arranged in a waffle pattern.

7. An arch support device, comprising:
a first, lower layer of semi-rigid material shaped to conform to the arch of a wearer's foot and to provide an arch supporting function when inserted in a shoe, the lower layer having a lower face for facing the sole of an item of footwear, an upper face, a heel region at one end, an arch region, and a toe region;
a second layer of cushioning material secured to the upper face of the lower layer;
a third, cover layer of pliable material secured over the second layer;

at least one of the first and second layers being of variable thickness; and the lower layer having an outer rim and the second and cover layers each having a peripheral rim extending outwardly beyond the outer rim of the lower layer around at least part of the periphery to form a projecting portion extending around the outer rim of the lower layer.

8. An arch support device, comprising:

a first, lower layer of semi-rigid material shaped to conform to the arch of wearer's foot and to provide an arch supporting function when inserted in a shoe, the lower lay having a lower face for facing the sole of an item of footwear, an upper face, a heel region at one end, an arch region, and a toe region;

a second layer of cushioning material secured to the upper face of the lower layer;

a third, cover layer of pliable material secured over the second layer;

at least one of the first and second layers being of variable thickness; and the lower layer having opposite heel and toe ends, and the foam and cover layers projecting beyond the toe end of the lower layer.

9. An arch support device, comprising:

a first, lower layer of semi-rigid material shaped to conform to the arch of a wearer's foot and to provide an arch supporting function when inserted in a shoe, the lower layer having a lower face for facing the sole of an item of footwear, an upper face, a heel region at one end, an arch region, and a toe region;

a second layer of cushioning material secured to the upper face of the lower layer;

a third, cover layer of pliable material secured over the second layer;

the lower layer being of variable thickness; and the second layer having a peripheral rim and the peripheral rim of the second layer being tapered outwardly from the lower layer to the cover layer.

* * * * *